US009384544B2

(12) United States Patent
Wright

(10) Patent No.: US 9,384,544 B2
(45) Date of Patent: Jul. 5, 2016

(54) METHOD AND APPARATUS FOR MEASURING A RATIO OF A VARIABLE IN MEDICAL IMAGING DATA

(71) Applicant: Thomas George Wright, Oxford (GB)

(72) Inventor: Thomas George Wright, Oxford (GB)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 13/650,311

(22) Filed: Oct. 12, 2012

(65) Prior Publication Data

US 2013/0096416 A1    Apr. 18, 2013

(30) Foreign Application Priority Data

Oct. 14, 2011    (GB) .................................. 1117804.3

(51) Int. Cl.
G06T 7/00    (2006.01)
G06T 7/40    (2006.01)
A61B 5/055    (2006.01)
A61B 6/03    (2006.01)

(52) U.S. Cl.
CPC .............. G06T 7/0012 (2013.01); G06T 7/401 (2013.01); A61B 5/055 (2013.01); A61B 6/037 (2013.01); G06T 2207/10104 (2013.01); G06T 2207/30016 (2013.01)

(58) Field of Classification Search
CPC ......... G06T 5/001; G06T 7/60; G06T 7/0075; G06T 7/0012

USPC .......... 600/407, 410, 411, 425, 436; 382/100, 382/181, 190, 191, 224
See application file for complete search history.

(56) References Cited

U.S. PATENT DOCUMENTS

| | | | | |
|---|---|---|---|---|
| 6,491,636 | B2 * | 12/2002 | Chenal et al. ................. | 600/450 |
| 2005/0283070 | A1 * | 12/2005 | Imielinska et al. ........... | 600/425 |
| 2007/0092132 | A1 | 4/2007 | Sato et al. | |
| 2009/0148022 | A1 * | 6/2009 | Lee et al. ...................... | 382/132 |
| 2009/0221881 | A1 | 9/2009 | Qian et al. | |
| 2010/0274134 | A1 | 10/2010 | Shyu et al. | |
| 2011/0170774 | A1 | 7/2011 | Lee et al. | |

FOREIGN PATENT DOCUMENTS

| | | |
|---|---|---|
| GB | 2451416 | 2/2009 |
| JP | 2011103070 | 5/2011 |
| WO | 2009/094044 | 7/2009 |

OTHER PUBLICATIONS

"An Improved Ration Edge Detector for Target Detection in SAR Images," Bai et al., IEEE Int. Conf. Neural Networks & Signal Processing, (2003) pp. 982-985.

* cited by examiner

Primary Examiner — Tse Chen
Assistant Examiner — Jason Ip
(74) Attorney, Agent, or Firm — Schiff Hardin LLP

(57) ABSTRACT

In a method and apparatus for measuring a ratio of a variable for assessment in medical imaging data of a subject, a viewable image is generated from source imaging data of the subject. A pair of regions of interest for arrangement on the viewable image is then generated, and a value of the variable for each region of the pair from the source imaging data is determined. The ratio of the two values is then determined from the pair.

15 Claims, 1 Drawing Sheet

METHOD AND APPARATUS FOR MEASURING A RATIO OF A VARIABLE IN MEDICAL IMAGING DATA

RELATED APPLICATION

The present application claims the benefit of the filing date of Provisional Application No. 61/547,202, filed Oct. 14, 2011.

BACKGROUND OF THE INVENTION

1. Field of the Invention

The present invention is directed to methods and apparatus for measuring a ratio of a variable for assessment in medical imaging data of a subject, in particular in MR and PET imaging data.

2. Description of the Prior Art

In the medical imaging field, several imaging schemes are known. For example PET (Positron Emission Tomography) is a method for imaging a subject in 3D using an injected radioactive substance which is processed in the body, typically resulting in an image indicating one or more biological functions. Other such functional imaging modalities are known, such as SPECT. Other modalities for example are Computed Tomography (CT) and Magnetic Resonance Imaging (MRI), known as anatomical imaging modalities.

In functional images, many important pathologies and anatomical structures appear as very high (or low) intensities. For example, a tumor in an FDG-PET image will often appear as a bright region.

For some types of medical image analysis, for example assessment of PET-florbetapir images for amyloid plaque deposition, it is useful to be able to quantify the ratio of uptake between areas of (specific) grey matter and (unspecific) white matter in the brain in a local neighborhood.

The most basic approach to solving this problem is to look visually at the image. However, problems of consistency can arise when different readers view the image, and in particular changing the window and level used to view the data can greatly affect the interpretation.

Alternatively, a user can manually create first and second regions of interest (ROIs), one in each part of the image to be quantified, and then calculate the ratio of the mean uptake in each of the regions. This approach provides quantification, but is time-consuming to perform, especially if multiple readings from different areas are required, as each reading requires interaction with the ROIs. In addition, if the areas to be investigated are small or thin (like the cortical grey matter), the ROIs can be hard to position precisely.

SUMMARY OF THE INVENTION

An object of the present invention is to address these problems and provide improvements upon the known devices and methods.

In general terms, an embodiment of a method according to the invention for measuring a ratio of a variable for assessment in medical imaging data of a subject, includes generating, in a processor, a viewable image from source imaging data of the subject, generating, in the processor, a pair of regions of interest for arrangement on the viewable image, determining, in the processor, a value of the variable for each region of the pair from the source imaging data, and determining, in the processor, a ratio of the two values from the pair.

This allows a simple way to immediately illustrate a ratio between two regions on the image, in which the calculation is performed from the source image data rather than from the re-constructed image, or from a combination of images used for the viewable image.

In an embodiment, the arrangement of the pair of regions on the viewable image is determined by a user.

Preferably, the pair of regions is arranged at a number of locations on the viewable image, values of the variable for the current location are dynamically determined, and the ratio is displayed to the user.

In another embodiment, the method further includes initially determining a set of values for arrangement of the pair of regions at each of a number of locations in the image, determining the ratio at each location, and identifying a location where the ratio is at a maximum.

Suitably, i) the respective sizes of, and/or ii) the separation distance between, the regions of the pair are determined by a pre-defined relationship.

Preferably, the pair of regions comprises a single super-region divided into the pair by a line or surface.

In embodiments, the imaging data comprises imaging data of the subject captured by anatomical and functional imaging modalities.

Preferably, the viewable image is generated from the anatomical imaging data, or from a combination of the anatomical imaging data with the functional imaging data; and the values are determined from the functional imaging data.

More preferably, the anatomical imaging modality is MR, and the functional modality is PET.

The invention also encompasses an apparatus for measuring a ratio of a variable for assessment in medical imaging data of a subject having a processor configured to generate a viewable image from source imaging data of the subject, generate a pair of regions of interest for arrangement on the viewable image, determine a value of the variable for each region of the pair from the source imaging data, and determine a ratio of the two values from the pair, and a display device at which the processor is configured to cause the viewable image with the ratio to be displayed.

The present invention also encompasses a non-transitory, computer-readable data storage medium encoded with programming instructions that, when the data storage medium is loaded into a processor, causes the processor to implement one or more of the embodiments of the inventive method described above.

DESCRIPTION OF THE PREFERRED EMBODIMENTS

When the following terms are used herein, the accompanying definitions can be applied:
PET—Positron Emission Tomography
SUV—Standardized Uptake Value
FDG—F-18 fluorodeoxyglucose, a PET radiotracer
MRI—Magnetic Resonance Imaging
ROI/VOI—Region/volume of interest.
CT—Computed Tomography Embodiments of the invention described herein concern a system to provide real-time quantification for looking at local contrast differences. The principles of the prevent invention, however, are not specific to amyloid imaging, but apply to any agent that is clinically assessed using visual assessment of local contrast.

The system measures a ratio of a variable for assessment, by generating a viewable image from source imaging data of the subject, having the user place a pair of regions of interest on the viewable image, but determining values of the variable for each region of the pair from the source imaging data itself (which are then used to determine the ratio of the values).

This allows quick quantification of the contrast ratio that the user is interested in knowing, particularly in assessment of amyloid plaques, provides instant updates of the ratio as the user moves the cursor, and provides quantification from the source data itself, rather than from the re-constructed or filtered image, or where the image is a combination and hence may be complicated by the combination.

Other features of embodiments of the invention may include:

real-time quantification for medical images producing a directional measure of local contrast around a point of interest in the image by: defining a point of interest in the image; defining a region of interest at said point of interest, that is divided into two parts by a dividing line; computing statistics in said parts; and orienting the dividing line such that the ratio of statistics computed in said parts is maximal.

In other embodiments:

the point of interest is determined from the position of the mouse cursor on the screen the region of interest is a circle divided into two semi-circular regions of equal area.

the statistics in the parts are the mean uptake within said part the region of interest corresponding to the maximal ratio is displayed on the screen.

the maximal ratio value is displayed on the screen near the point of interest.

Figure 1:
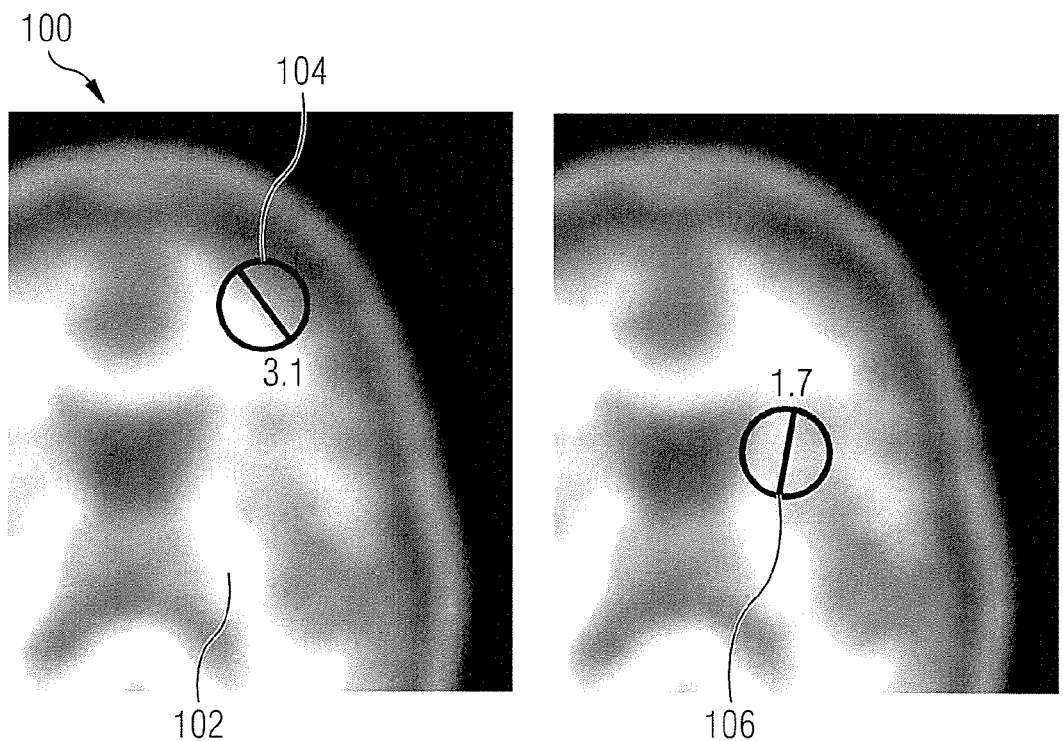
FIG. 1 illustrates placement of the regions of interest according to an embodiment of the invention.

Embodiments of the invention described here can provide a tool that works as follows, with reference to FIG. 1 a patient brain image, with the new tool overlaid:

the system displays a circular ROI (104, 106), divided into two halves, and overlaid on the image (100) of the brain (102)

the system displays the ratio of the mean uptake in each half of the circle to the user—for example for the first ROI pair shown in FIG. 1 (104), the ratio of the mean uptake is 3.1 (as shown next to the ROI pair 104)

the orientation of the line sub-dividing the circle is determined algorithmically (see below for details) to maximize the ratio of mean uptake in the two halves as the user moves the mouse, the position of the center of the circle follows the mouse cursor, and the orientation of the circle is dynamically updated to produce the maximum contrast ratio. For example, ROI pair 106 in FIG. 1 is at a second position of the cursor (as the central point has moved), but the orientation of the dividing line has been automatically determined to be different, as this produces the greatest contrast ratio for this cursor point. The new ratio value 1.7 is indicated next to the ROI pair 106.

The left image of the two images in FIG. 1 shows the (maximum) ratio in a relatively high-contrast region, the right image the ratio in a lower-contrast region.

There are many algorithms that could be used to determine the orientation of the tool, although it must be considered that the intention is to update the orientation in real time as the user moves the mouse, so there is a limit on the amount of computation that can be performed. One of the most straightforward approaches is to perform a brute-force search of all rotation angles from 0 to 180 degrees in, for example, thirty-six 5 degree increments, working out the mean intensity in each half of the circle for each increment, and then choosing the value that maximizes the ratio. When working with this tool in a 2D slice of an image, this approach is easily fast enough for interactive display.

By ensuring that the algorithm works in real time, the user is able to use this tool to inspect the dataset, and get results quickly just by moving the mouse around.

Unlike the basic visual method, the quantification is independent of the window and level applied to the data, and independent of the individual performing the analysis (at least, the system will display the same ratio if the tool is placed at the same position on the image). Unlike the manual ROI method, due to the real-time feedback, it is possible for the user to move the cursor over the image and get a feel for the local contrast throughout the image, in an analogous way to a physicist understanding the field of a magnet by moving a compass around.

In an alternative embodiment, the system can adjust the size and shape of the circle, for example using an ellipse or rectangle. Particular shapes could be more appropriate to certain problems—for example an elongated ellipse (divided along its long axis) may be most appropriate when the two areas of local intensity being compared are very thin, but relatively straight. Alternatively, if structures of a particular shape are being investigated, a custom shape tailored for those structures may provide the best results.

For certain problems and structures, it may be useful to divide the shape asymmetrically, so that the two pieces are not the same size; indeed, the dividing line need not even be straight.

Embodiments of the invention can be applied in three dimensions, using a sphere or other three dimensional shape. Here, the dividing "line" would actually be a plane, splitting the shape into two pieces.

For certain problems, it may be desirable to separate the two pieces of the ROI, while keeping them at a fixed distance apart, or even allowing them to move relative to each other (for example within a specific restricted window, where the position is automatically determined to maximize the contrast ratio).

Rather than basing the position of the mouse directly on the image to be quantified as described above, the tool could work on a fused view (e.g., of MR overlaid with PET data), with the user basing the position of the centre of the tool on features from the MRI (e.g., grey-matter/white-matter boundary), and quantifying from the PET data, which may reduce bias of the reader to focus on areas of high contrast in the PET image rather than areas of different tissue types.

In addition to the previous embodiment, the tool can be modified to search for the maximal contrast area within a window around the cursor, essentially "snapping" to that position. This "snapping" functionality can be driven from the data being quantified, or alternatively it can be driven by an auxiliary dataset (for example the MR dataset described previously). Depending on the type of the auxiliary dataset, other techniques than maximal contrast could be used to drive the position the tool would "snap" to.

Figure 2:
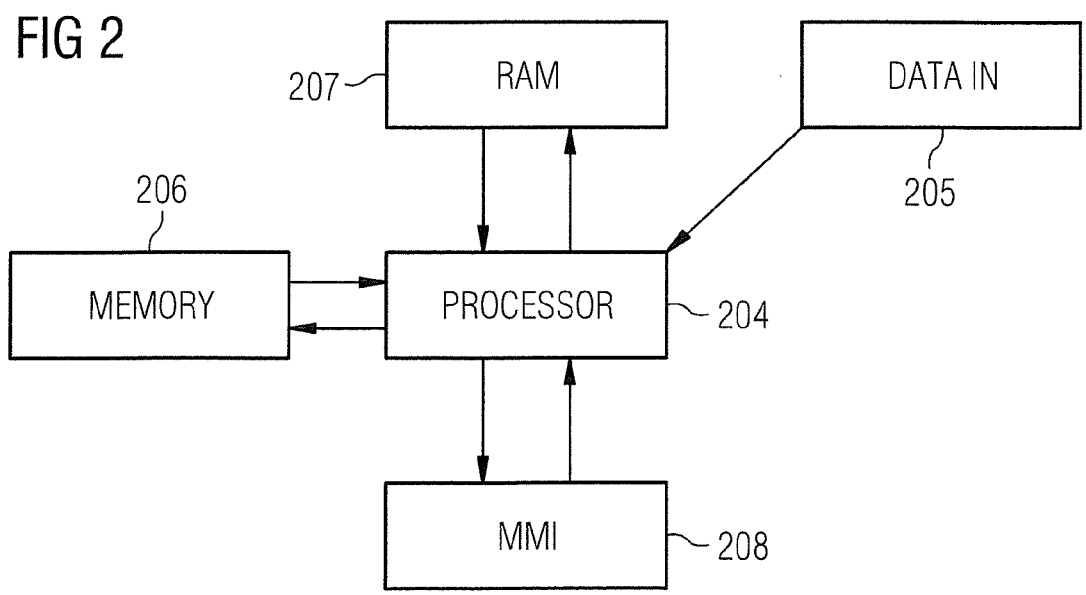
FIG. 2 illustrates an apparatus according to an embodiment of the invention.

Referring to FIG. 2, the above embodiments of the invention may be conveniently realized as a computer system suitably programmed with instructions for carrying out the steps of the methods according to the invention.

For example, a central processing unit 204 is able to receive data representative of medical scans via a port 205 which could be a reader for portable data storage media (e.g. CD-ROM); a direct link with apparatus such as a medical scanner (not shown) or a connection to a network.

Software applications loaded on memory 206 are executed to process the image data in random access memory 207.

The processor 204 in conjunction with the software can perform the steps such as generating a viewable image from source imaging data of the subject; generating a pair of regions of interest for arrangement on the viewable image; determining a value of the variable for each region of the pair from the source imaging data; and determining a ratio of the two values from the pair.

A Man—Machine interface 208 typically includes a keyboard/mouse/screen combination (which allows user input such as initiation of applications) and a screen on which the results of executing the applications are displayed.

Although modifications and changes may be suggested by those skilled in the art, it is the intention of the inventor to embody within the patent warranted hereon all changes and modifications as reasonably and properly come within the scope of his contribution to the art.

I claim as my invention:

1. A computerized method to automatically quantify a spatially variable biological feature of an examination subject, comprising:
   providing a computerized processor with source data obtained from an examination subject, said source data representing a spatially variable biological feature of the examination subject, selected from the group consisting of anatomical features and dynamic physiological features;
   in said processor, executing an image reconstruction algorithm on said source data to generate an image, comprised of image elements, of said examination subject, in which said spatially variable biological function is represented by correspondingly spatially varied brightness of respective image elements;
   from said processor, displaying said image at a viewing screen;
   via a user interface of said processor, causing a visible, continuous outline, having a predetermined outline size, to move to a selected position within said image at said viewing screen;
   in said processor, automatically dividing an area of said image at said viewing screen, surrounded by said outline, into two contiguous outlined areas divided by a continuous border shared by said two contiguous outlined areas that proceeds through said continuous outline;
   in said processor, automatically calculating, from source data represented by image elements in a first of said two outlined areas, a first value of said biological feature, and calculating, from source data represented by image elements in a second of said two outlined areas, a second value of said biological feature, and calculating a ratio of said first value and said second value, by automatically successively rotating said border through a plurality of rotational angles and calculating said first value and said second value and said ratio with said border respectively at each of said rotational angles, and selecting a numerical value of said ratio that is the maximum value of said ratio among the respective ratios calculated for each of the rotational angles of said border; and
   from said processor, displaying said numerical value of said ratio at said viewing screen simultaneously with said visual outline at said selected position.

2. A method as claimed in claim 1 comprising:
   via said user interface, causing said visual outline to move successively to a plurality of different positions within said image at said viewing screen;
   at each of said positions, calculating said first value, said second value and said ratio; and
   while said visible outline is present at each of said different positions on said viewing screen, displaying the respective numerical value of the ratio calculated for that respective position at the display screen.

3. A method as claimed in claim 2 comprising causing said visible outline to successively move to said different positions at said viewing screen by manually entering, via said user interface, a set of positions designating said plurality of different positions.

4. A method as claimed in claim 2 comprising causing said visible outline to successively move to said different positions at said viewing screen by manually controlling a curser, via said user interface.

5. A method as claimed in claim 1 comprising causing said visible outline to move to said selected position within said image at said viewing screen by manually controlling a cursor, via said user interface.

6. A method as claimed in claim 1 comprising setting and storing said predetermined size of said visible outline automatically in said processor.

7. A method as claimed in claim 1 comprising setting said predetermined size of said visible outline manually via said user interface.

8. A method as claimed in claim 1 comprising reconstructing said image as a two-dimensional image.

9. A method as claimed in claim 1 comprising reconstructing said image as a three-dimensional image.

10. A method as claimed in claim 1 comprising providing said computerized processor with data, as said source data, obtained from an imaging modality selected from the group consisting of anatomical imaging modalities and functional imaging modalities.

11. A method as claimed in claim 1 comprising providing said computerized data with data, as said source data, obtained from an imaging modality selected from the group consisting of a magnetic resonance apparatus and a positron emission tomography apparatus.

12. A method as claimed in claim 1 comprising:
   providing said computerized processor with source data comprising both anatomical data and functional imaging data;
   reconstructing said image from both said anatomical data and said functional imaging data so that both said anatomical data and said functional imaging data are represented by said image elements of said image at said viewing screen; and
   calculating said first value and said second value only from the functional imaging data of the source data represented by the image elements respectively within said first of said outlined areas and said second of said outlined areas.

13. A method as claimed in claim 1 comprising:
   forming said visible outline on said viewing screen as a circle having said predetermined size, and automatically dividing said circle into said two contiguous outlined areas by designating, as said border, a diameter of said circle, within said circle, at said viewing screen;

in said processor, with said circle at said selected position, automatically successively rotating said diameter through a plurality of rotational angles and calculating said first value and said second value and said ratio with said diameter respectively at each of said rotational angles; and in said processor, selecting, as said numerical value of said ratio for display at said viewing screen, the maximum value of said ratio among the respective ratios calculated for each of said rotational angles of said diameter.

14. A computerized workstation for manually evaluating medical image data, said workstation comprising:

a computerized processor;

a user interface in communication with said computerized processor configured to operate said computerized processor according to entries made via said user interface;

a display unit in communication with said computerized processor, said display unit comprising a viewing screen;

said computerized processor having a data input that receives source data obtained from an examination subject, said source data representing a spatially variable biological feature of the examination subject, selected from the group consisting of anatomical features and dynamic physiological features;

said processor being configured to execute an image reconstruction algorithm on said source data to generate an image, comprised of image elements, of said examination subject, in which said spatially variable biological function is represented by correspondingly spatially varied brightness of respective image elements;

said processor being configured to display said image at a viewing screen;

said user interface of said processor being configured to cause a visible, continuous outline, having a predetermined outline size, to move to a selected position within said image at said viewing screen;

said processor being configured to automatically divide an area of said image at said viewing screen, surrounded by said outline, into two contiguous outlined areas divided by a continuous border shared by said two contiguous outlined areas that proceeds through said continuous outline;

said processor being configured to automatically calculate, from source data represented by image elements in a first of said two outlined areas, a first value of said biological feature, and to calculate, from source data represented by image elements in a second of said two outlined areas, a second value of said biological feature, and to calculate a ratio of said first value and said second value, by automatically successively rotating said border through a plurality of rotational angles and calculating said first value and said second value and said ratio with said border respectively at each of said rotational angles, and selecting a numerical value of said ratio that is the maximum value of said ratio among the respective ratios calculated for each of the rotational angles of said border; and said processor being configured to display a numerical value of said ratio at said viewing screen simultaneously with said visual outline at said selected position.

15. A non-transitory, computer-readable data storage medium encoded with programming instructions, said data storage medium being loaded into a computerized processor of a medical image data viewing system that comprises a display screen and a user interface, said programming instructions causing said computerized processor to:

receive source data obtained from an examination subject, said source data representing a spatially variable biological feature of the examination subject, selected from the group consisting of anatomical features and dynamic physiological features;

execute an image reconstruction algorithm on said source data to generate an image, comprised of image elements, of said examination subject, in which said spatially variable biological function is represented by correspondingly spatially varied brightness of respective image elements;

display said image at a viewing screen;

via a user interface of said processor, cause a visible, continuous outline, having a predetermined outline size, to move to a selected position within said image at said viewing screen;

automatically divide an area of said image at said viewing screen, surrounded by said outline, into two contiguous outlined areas divided by a continuous border shared by said two contiguous outlined areas that proceeds through said continuous outline;

automatically calculate, from source data represented by image elements in a first of said two outlined areas, a first value of said biological feature, and calculate, from source data represented by image elements in a second of said two outlined areas, a second value of said biological feature, and calculate a ratio of said first value and said second value, by automatically successively rotating said border through a plurality of rotational angles and calculating said first value and said second value and said ratio with said border respectively at each of said rotational angles, and selecting a numerical value of said ratio that is the maximum value of said ratio among the respective ratios calculated for each of the rotational angles of said border; and display a numerical value of said ratio at said viewing screen simultaneously with said visual outline at said selected position.

* * * * *